United States Patent
Chang et al.

(10) Patent No.: US 6,717,146 B2
(45) Date of Patent: Apr. 6, 2004

(54) TANDEM MICROCHANNEL PLATE AND SOLID STATE ELECTRON DETECTOR

(75) Inventors: Tai-Hon Philip Chang, Foster City, CA (US); Stuart L. Friedman, Palo Alto, CA (US); Ming L. Yu, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 100 days.

(21) Appl. No.: 09/866,361

(22) Filed: May 24, 2001

(65) Prior Publication Data

US 2002/0175283 A1 Nov. 28, 2002

(51) Int. Cl.⁷ .............................. G03G 13/00; G01T 1/24
(52) U.S. Cl. ............................ 250/315.3; 250/370.11; 250/397
(58) Field of Search .................. 250/315.3, 370.11, 250/397

(56) References Cited

U.S. PATENT DOCUMENTS

| | | | |
|---|---|---|---|
| 4,891,829 A | * 1/1990 | Deckman et al. | 378/4 |
| 4,958,079 A | 9/1990 | Gray | |
| 5,475,225 A | * 12/1995 | Stettner | 250/370.11 |
| 5,804,833 A | * 9/1998 | Stettner et al. | 257/10 |
| 5,854,506 A | * 12/1998 | Fallica | 257/429 |
| 5,990,483 A | * 11/1999 | Shariv et al. | 250/397 |
| 6,133,989 A | * 10/2000 | Stettner et al. | 356/4.01 |
| 6,355,420 B1 | * 3/2002 | Chan | 435/6 |

FOREIGN PATENT DOCUMENTS

| | | | |
|---|---|---|---|
| DE | 0768700 | * 4/1997 | H01J/37/244 |
| EP | 0 768 700 A | 4/1997 | |
| FR | 2 597 254 A | 10/1987 | |

OTHER PUBLICATIONS

Marconi, "Fast Gating of a Windowless Dual–Multichannel–Plate–Intensified Array Detector," *Journal of Physics E. Scientific*, Bristol, GB, vol. 22, No. 10, Oct. 1, 1989, pp. 849–852.

Patent Abstracts of Japan, vol. 008, No. 033 (P–254), Feb. 14, 1984 (JP 58 189574 A).

Patent Abstracts of Japan, vol. 013, No. 203 (P–870) May 15, 1989 (JP 01 023146 A).

* cited by examiner

Primary Examiner—John R. Lee
Assistant Examiner—Paul Gurzo
(74) Attorney, Agent, or Firm—Sughrue Mion

(57) ABSTRACT

A compact detector for secondary and backscattered electrons in a scanning electron beam system includes a microchannel plate detector and a solid state detector connected in a tandem manner. The detector offers large bandwidth and high dynamic range. The detector can be used for article inspection, lithography, metrology, and other related applications. The compactness of the detector makes it ideally suited for utilization in a miniature electron beam column, such as a microcolumn.

21 Claims, 2 Drawing Sheets

TANDEM MICROCHANNEL PLATE AND SOLID STATE ELECTRON DETECTOR

BACKGROUND OF THE INVENTION

1. Field of the Invention

This invention generally relates to design of electron detectors. Specifically, this invention relates to design of tandem microchannel plate and solid state electron detector having a high linearity of the amplification coefficient over a wide dynamic range of the input current signal.

2. Description of the Related Art

In a conventional scanning beam apparatus, a specimen under inspection is irradiated with a particle beam called a primary beam. For example, the irradiating primary particle beam can be an electron beam. The interaction of the primary particle beam with the specimen causes the specimen to emit electrons with kinetic energies ranging between zero electron-volts (eV) and the kinetic energy of the particles in the primary beam.

The electrons emitted by the specimen are classified according to their initial kinetic energies. The first group of electrons, with kinetic energies of up to 50 eV is called secondary electrons, or secondaries. The secondary electrons emitted by the specimen typically carry information about the topographical structure of the specimen.

The interaction of the primary beam with the specimen also causes the emission of a second class of electrons, called backscattered electrons. The backscattered electrons have energies ranging from 50 eV and up to the kinetic energy of the particles (electrons) in the primary beam and carry information about the topographical structure and the material composition of the specimen.

The secondary and backscattered electrons emitted by the specimen are collected using an electron detector. It should be noted that most of the existing electron detectors are capable of detecting only electrons with kinetic energies included in a predetermined detection energy range. In addition, the detection efficiency (the ratio of the number of detected electrons to the total number of secondary and backscattered electrons emitted from the specimen) generally increases with the increase of the electron energy. Accordingly, in order to detect the secondary and backscattered electrons with higher efficiency, it is advantageous to increase their kinetic energies. Typically, this is accomplished by accelerating the electrons in the electric field of the scanning beam apparatus. The aforementioned accelerating electric field can be produced by biasing the surface of the specimen and the surface of the electron detector, such as to create a suitable electric potential difference therebetween.

The aforementioned electron detector collects the electrons emitted by the specimen and generates an output electrical signal representative of the cumulative charge of the collected electrons, multiplied by the amplification factor of the detector. The electric signal produced by the electron detector is used in creating an image of the specimen. Depending on the nature of the electrons used in imaging (secondary or backscattered), the created image is indicative of the topographic and/or the material structure of the specimen. After the image of the area of the specimen irradiated by the primary beam spot is created using the secondary and/or backscattered electrons, the specimen is moved with respect to the irradiating primary electron beam so that the scanning beam apparatus can produce an image of the next area. The specimen can be moved in a continuous or stepwise manner.

Unfortunately, when the secondary and backscattered electrons emitted by the specimen are detected by a detector, the "transit time" between the arrival of the detected electron and the collection of the amplified signal at the other side of the detector can vary, sometimes substantially. A wide variation in the transit time results in the decrease of the frequency response of the detector. That subsequently decreases the scanning speed of the particle beam apparatus because the apparatus has to "wait" for the signal emitted by the irradiated spot of the specimen to clear the detector, before it can move on to scan the next spot. Because the width of the transit time distribution is proportional to the average electron travel time through the detector, it is advantageous to minimize the electron travel time by accelerating electrons in an electric field and/or by reducing the travel distance of the electrons.

Accordingly, in order to minimize the spread of the detector transit time in a scanning beam apparatus, the detector of the secondary and backscattered electrons preferably has a low profile so that it does not add significantly to the overall length of the electron travel path.

One type of electron detector which is presently used for detecting electrons in microcolunms is a microchannel plate (MCP) electron detector. The microchannel plate detector comprises a thin plate, typically manufactured from an insulating material, such as glass. For example, the plate can be a few hundred microns thick. The plate of the microchannel plate detector contains a plurality of thin, typically round channels, which pass through the bulk of the plate and connect the opposite faces of the plate. The inside surfaces of these channels are coated with a material having a good secondary electron emission coefficient. A potential difference is applied between the two faces of the microchannel plate to create an accelerating electric field inside the channels.

A typical microchannel plate detector can be used to amplify the input current signal with a gain of up to tens of thousands. The amplification factor of the microchannel plate detector has such a high value for the following reasons. First, as well known to persons of skill in the art, when an electron strikes a working surface of the microchannel plate detector, it releases additional electrons, the number of which goes up with the kinetic energy of the striking electron, to about 1 keV. To maximize the number of the released electrons, the working surface of the microchannel plate detector is manufactured of, or coated with a material having a good secondary emission coefficient. It will also be appreciated by those of skill in the art that before striking the working surface of the microchannel plate, the secondary and backscattered electrons emitted by the specimen under examination are accelerated by the electric field of the microcolumn to a few hundred eV, or more.

Second, the electrons released from the working surfaces of the microchannel plate travel through the channels of the detector being accelerated in the electric field created by a potential difference applied to the opposite faces of the microchannel plate. During their travel inside the channels of the microchannel plate detector, the electrons strike the inside surfaces thereof, releasing greater and greater numbers of additional electrons. These additional electrons are also accelerated and strike the walls, which results in the production of even greater numbers of electrons. Accordingly, the described avalanche-like electron production results in exceptionally high signal amplification in the microchannel plate detector.

Because the number of the electrons released in each collision is related to the energy of the striking electron, the amplification factor of the microchannel plate detector depends on the potential of the front face of the detector with respect to the specimen, and the potential difference applied to the opposite faces of the detector.

The electronic current signal amplified by the microchannel plate is collected by a collector electrode and measured by a current monitor. A 100 pA input signal can give a 1 microamp output current at a gain of 10,000. Due to the aforementioned exceptionally high gain of the microchannel plate detector, detection of the input signals down to 1 pA is routinely possible. A major drawback of the microchannel plate detector is that its output current is substantially limited. When the output current of the detector exceeds about 10% of the microchannel plate strip current, the gain of the microchannel plate decreases causing the amplification factor of the device to be nonlinear. A typical strip current for the microchannel plate detector used in the described microcolumn is about 10 microamps. At a gain of 10,000, for a 1 microamp output current, the input current signal should not exceed 100 pA, for good linearity. To maintain linearity in the 10 nA input current signal range, the gain has to be below 100. Therefore, to maintain a good linearity and avoid saturation of the microchannel plate at high input electron currents, the gain of the microchannel plate has to be reduced so that the output signal of the microchannel plate does not exceed its upper linearity limit, or 10% of the microchannel plate strip current. Accordingly, the microchannel plate detector is not suitable for operating at high signal gains and high input current signals.

Accordingly, the dynamic range of the input electron current signal in the microchannel plate detector is substantially limited. As well known to persons of skill in the art, the term dynamic range of the microchannel plate refers to the ratio of the highest input electron current, which can be amplified by the microchannel plate in a linear manner to the lowest detectable electron current.

Accordingly, there exists a need for, at it would be advantageous to have a compact electron detector, which would offer a large bandwidth and high linearity of the amplification factor in a wide dynamic range of the input current signal. Such detector could be used as a detector for secondary and backscattered electrons in a scanning electron beam system for inspection, lithography, metrology, and other related applications.

SUMMARY OF THE INVENTION

It is one feature of the present invention to provide a compact detector for secondary and backscattered electrons in a scanning particle beam system, to provide high linearity of the amplification over a wide dynamic range of the input current signal. The compactness of the detector makes it ideally suited also for miniature electron beam columns such as microcolumns.

To achieve the above and other benefits and advantages of the present invention, there is provided a tandem electron detector for detecting secondary and backscattered electrons. The inventive tandem electron detector comprises a solid state detector and a microchannel plate detector.

BRIEF DESCRIPTION OF THE DRAWINGS

These and other features and benefits of the invention will be readily appreciated in the light of the following detailed description of preferred embodiments thereof, given by way of example only with reference to the accompanying drawings wherein.

DETAILED DESCRIPTION OF A PREFERRED EMBODIMENT

Figure 1:
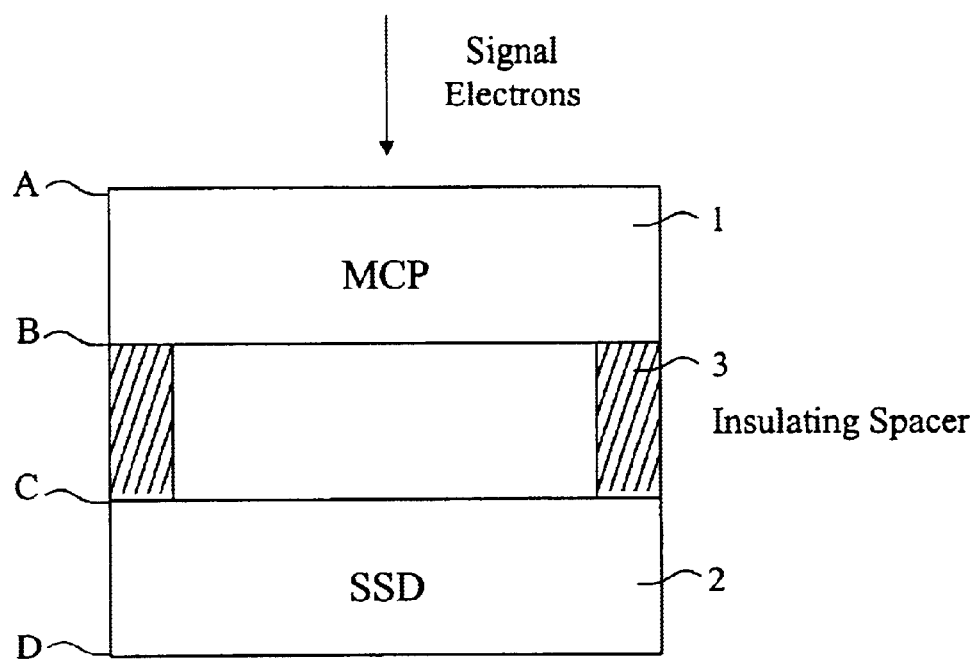
FIG. 1 shows a schematic structure of the inventive tandem electron detector.

A preferred embodiment of the inventive tandem electron detector now will be described with reference to the attached drawings, wherein identical elements are designated with like numerals.

Recently, it has been shown that solid state detectors (SSD) in the form of p-n junctions or charge coupled devices (CCD) can be used to detect electrons with kinetic energies in the keV range. Electrons in this energy range are of interest, for example, in particle beam imaging systems comprising microcolumns. The aforementioned solid state detectors are commonly manufactured in a thin parallel plate geometry similar to the microchannel plate detectors described above.

At the present time, so far as the present inventors are aware, there exist no electron detectors which combine a microchannel plate and a solid state detector in a single detector assembly. The only known combination of the microchannel plate and solid state detector is a charge-coupled device (CCD) image intensifier. In the aforementioned imaging application, the electron current is first amplified by the microchannel plate. The amplified electron signal forms an optical image on a phosphor screen. This optical image is then recorded by a CCD solid state detector. However, presently there are no devices which use the microchannel plate to amplify the input electron signal, and a solid state detector to detect this amplified signal.

A solid state detector for electron detection is similar to a p-n junction photodiode. An incident electron, like a photon, uses its energy to produce a plurality of electron-hole pairs in a bulk of silicon. These electrons and holes drift in an electric field inside the detector to their respective electrodes, wherein they are collected and converted into electrical signals. Thereby, an output current signal proportional to the energy dissipated by the striking electron is generated from the electron-hole pairs and output into subsequent signal processing stages, such as pre-amplification, amplification, and signal shaping circuits. Therefore, the solid state detecting device potentially can be used in a microcolumn for detecting secondary and/or backscattered electrons.

However, solid state detectors have certain limitations. As is well known in the art, it takes approximately 3.7 eV to create an electron-hole pair in silicon. Therefore, for 1 keV striking electrons, the electron amplification factor of the silicon detector is only about 270. This amplification is significantly lower than that of a microchannel plate detector, which can be about 10,000 at low input signal currents. The actual gain of the solid state detector is even lower because the energy of the striking electron is also dissipated on the contaminants and protective layers on top of the solid state detector. For all the foregoing reasons, at low signal currents, the detection sensitivity of a solid state detector is inferior to that of a microchannel plate detector. However, the solid state detector has one significant advantage over the microchannel plate detector. In particular, linearity over a dynamic range of nine orders of magnitude has been achieved for this type of detector. Importantly, the output signal linearity can be maintained at output currents above 100 microamps. Accordingly, the maximum output current in the linearity region of the solid state detector is two orders of magnitude higher than that of the microchannel plate detector. The linearity of the output signal of the solid state detector is limited only by the current loading of the device. The value of the upper limit on the input current signal increases with the increase of the reverse bias voltage and the decrease of the load impedance.

In contrast to the known electron detection systems, the inventive electron detector uses a microchannel plate detector and a solid state detector arranged in a tandem assembly. Specifically, the invention uses the high gain of the microchannel plate to amplify low current input signals. For good linearity at high input currents, the gain of the solid state detector is used to supplement the gain of the microchannel plate detector so that the latter can operate at low gain. Therefore, this tandem detector can be used over a larger dynamic range of the input current signal.

As will be appreciated by those of skill in the art, the microchannel plate is used by the present invention not as an electron detector, but as an electron signal amplifier. Therefore, the electrons are not being collected by the microchannel plate, but pass through the microchannel plate towards the solid state detector.

By way of example, and not by way of limitation, the inventive detector can be used for article inspection, lithography, and metrology, as well as in many other related applications. The compactness of the detector makes it ideally suited for use in miniature electron beam columns, such as microcolumns.

According to the present invention as shown in FIG. 1, a microchannel plate 1 and a solid state detector 2 are arranged according to a parallel plate geometry. Electrical contacts are placed at the front (A) and back (B) surfaces of the microchannel plate 1, and also at the two terminals (C) and (D) of the solid state detector 2. The microchannel plate 1 and the solid state detector 2 are separated from each other by a thin insulating ring 3. For example, and not as a limitation, the width of the gap between the microchannel plate detector 1 and the solid state detector 2 can be about 100 microns. Such a short distance between the microchannel plate and the solid state detector provides for short electron travel path in the detector.

Figure 2:
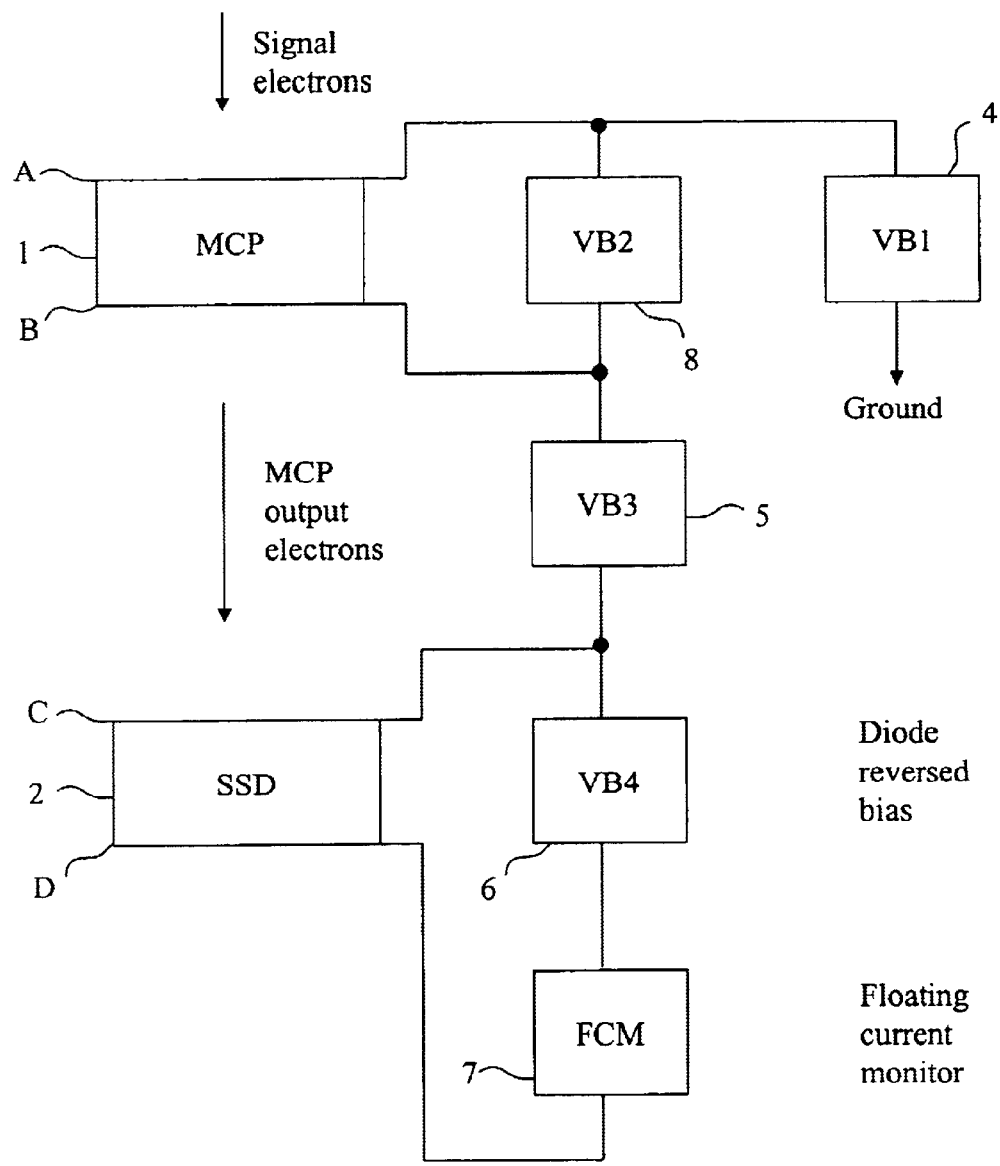
FIG. 2 illustrates the supply of bias voltages to the detector.

The principle of operation of the inventive tandem electron detector is illustrated in FIG. 2. As shown in this figure, the gain of the microchannel plate detector 1 is determined by the two bias voltages VB1 and VB2, supplied by voltage sources 4 and 8, respectively. The voltage VB1 supplied by the voltage source 4 controls the arrival energy of the signal electrons, which, as described above, determines the conversion gain at the front face A of the microchannel plate 1. The back side B of the microchannel plate 1 is biased positively with respect to the front side A, VB2 being the potential difference across the microchannel plate 1. The bias voltage VB2 supplied by the voltage source 8 determines the signal gain across the microchannel plate 1, as has been described above. Preferably, the value of the voltage VB2 is in the range between a few hundred volts and 1 kilovolt. As a result, the cumulative gain of the microchannel plate detector 1 is a product of the aforementioned two gains and is controlled by both bias voltages VB1 and VB2.

As is well known in the art, a solid state detector (SSD) exhibits the electrical characteristics of a diode. FIGS. 1 and 2 show such a solid state detector 2 having two electrical terminals C and D. This detector 2 is biased positively by a voltage VB3 with respect to the back side B of the microchannel plate 1. The voltage VB3 is provided by a voltage source 5. The described arrangement provides for additional acceleration of the electrons output by the microchannel plate 1 and permits the solid state detector 2 to collect these output electrons. The value of the voltage VB3 determines the energy of the electrons striking the solid state detector 2. On the other hand, because the energy of electrons striking the front surface of the solid state electron detector 2, in turn, determines the number of electron-hole pairs released by them, the voltage VB3 also controls the gain of the solid state detector 2. The value of the voltage VB3 in a microcolumn can be as high as several kilovolts. The solid state detector 2 is also biased, as a reverse bias diode, by a voltage VB4, supplied by a voltage source 6 and applied between the two terminals C and D of the solid state detector 2, as shown in FIG. 2. A floating current monitor (FCM) 7 connected in series with the solid state detector 2 measures the output current thereof. The aforementioned biasing voltage VB4 has two main functions. In particular, the reverse biasing voltage VB4 provides for better frequency response and higher linear output current of the solid state detector 2. It should be noted that the frequency response of the inventive tandem detector is limited by the frequency response of both the microchannel plate detector 1 and the solid state detector 2. The voltage VB4 usually has a value on the order of a few tens of volts.

As will be appreciated by those of skill in the art, for very low signal current, the microchannel plate detector 1 should operate at high gain. The gain of the microchannel plate detector can be adjusted, for example, by adjusting the voltage VB2, applied to the opposite sides thereof. Alternatively, this gain may be adjusted by adjusting the voltage VB1 generated by voltage source 4. The voltage VB3 also can be adjusted to provide for a high gain in the solid state detector 2 and to ensure optimal detection sensitivity thereof.

For intermediate values of the input current signal, the present invention uses the solid state detector 2 to provide for linear amplification over a large dynamic range of the input current signal. The voltages VB3 and VB4 biasing the solid state detector are adjusted such as to provide for a high amplification factor of the solid state detector 2. The gain of the microchannel plate detector 1 is lowered such that the microchannel plate detector remains in the linear signal region. In other words, as the input signal amplitude increases, the gain of the microchannel plate detector should be decreased such that the detector remains in the linear region at the maximum input signal current. Any loss of the overall gain of the tandem detector can be compensated by increasing the gain of the solid state detector 2 by increasing the value of the voltage VB3.

Finally, for high input signal current, the gain of the microchannel plate 1 is lowered even further such that the detector remains in the linear range. The gain of the solid state detector 2 may also need to be lowered such that the output current thereof does not exceed the upper boundary of the linear amplification region of the solid state detector 2.

As will be appreciated by those of skill in the art, the values of the gains of the microchannel plate and the solid state detector are determined by the particular application wherein the inventive tandem detector is utilized. Typically, a given application requires a certain signal to noise ratio (SNR) at a certain bandwidth. The electronic preamplifier used to amplify the electric signal at the output of the electron detector introduces a certain amount of additive noise at the required bandwidth. Given that noise and the required SNR, the required signal level at the preamplifier input is determined as a product of the SNR and the preamplifier equivalent input noise. It should be noted that the preamplifier equivalent input noise is an amount of noise which should be introduced at the input of an ideal (noiseless) preamplifier in order to produce the output noise level of the real preamplifier.

The preamplifier input signal level (the signal level at the output of the electron detector) and the initial electron signal level (the signal level at the input of electron detector) determine the required gain of the inventive electron detector. In general, a solid state detector does not have a sufficient gain. A microchannel plate detector provides sufficient gain; however, the required preamplifier input signal level may be close to, or may even exceed the output saturation current of the microchannel plate. This shortcoming of an electron multiplier will be present regardless of the initial signal level and hence regardless of gain. As the result, the dynamic range of the input signal is very limited.

To solve this problem, the present invention uses a solid state detector as a gain stage between the electron multiplier output and the preamplifier input. If the solid state detector has enough gain, the signal at the output thereof will be high enough to be put into the preamplifier, while the output signal of the microchannel plate will no longer exceed its maximum linear output current.

The solid state detector may in fact have more gain than this and thus may provide added flexibility. However, a relevant consideration is that the solid state detector can boost a reasonable output signal of the microchannel plate to the required pre-amp input regardless of the initial signal level and the operating gain of the microchannel plate.

Finally, it should be noted that the gain of the microchannel plate can be adjusted depending on the input signal level. To some extent, both the gain of the microchannel plate and the gain of the solid state detector may be adjusted to optimize noise, bandwidth and reliability. However, the gain of the solid state detector must always be such that the microchannel plate operates with an output current below its limit.

Under certain circumstances, the terminals C and D of the solid state detector 2 can be tied together and the solid state detector 2 can be used as a Faraday plate for collecting the output electron current from the microchannel plate 1. Such configuration should be used when the full frequency response of the microchannel plate 1 is required and the signal is sufficiently large such that the gain of the solid state detector 2 is unnecessary.

Although the invention has been described herein with reference to preferred embodiments thereof, it will be appreciated by those of skill in the art that numerous modifications in form and detail can be effected therein without departing from the scope and spirit of the invention as defined in and by the appended claims.

What is claimed is:

1. A method for detecting input electrons, said method comprising:
    (a) amplifying a current signal corresponding to said input electrons using a microchannel plate to produce an amplified current signal; and
    (b) detecting said amplified current signal using a solid state detector,
        wherein the gain of said microchannel plate is adjusted based on an amplitude of said current signal to substantially maintain linearity of amplification.

2. The method of claim 1, wherein said amplifying comprises accelerating said input electrons before they strike a working surface of said microchannel plate.

3. The method of claim 1, wherein said amplifying comprises providing said microchannel plate with a working surface, wherein said input electrons striking said working surface produce second generation electrons.

4. The method of claim 3, wherein a number of said second generation electrons is greater than a number of said input electrons striking said working surface.

5. The method of claim 3, wherein said amplifying further comprises accelerating said second generation electrons inside channels of said microchannel plate.

6. The method of claim 3, wherein said amplifying comprises providing inside surfaces of channels of said microchannel plate, wherein said second generation electrons strike said inside surfaces to produce third and higher generation electrons, said amplified current signal comprising said third and higher generation electrons.

7. The method of claim 6, wherein a number of said third and higher generation electrons is greater than a number of said second generation electrons.

8. The method of claim 7, further comprising accelerating said third and higher generation electrons between said microchannel plate and said solid state detector.

9. The method of claim 1, wherein said (b) comprises electrically connecting opposite faces of said solid state detector.

10. A tandem detector for detecting input electrons, said detector comprising:
    (a) a microchannel plate for amplifying a current signal corresponding to said input electrons to provide an amplified current signal; and
    (b) a solid state detector for detecting said amplified current signal,
        wherein the gain of said microchannel plate is adjusted based on an amplitude of said current signal to substantially maintain linearity of amplification.

11. The tandem detector of claim 10, further comprising a first voltage source for biasing a front face of said microchannel plate to accelerate said input electrons before said input electrons strike a front face of said microchannel plate.

12. The tandem detector of claim 11, wherein said front face of said microchannel plate comprises a coating, said input electrons incident on said coating producing second generation electrons.

13. The tandem detector of claim 12, wherein said microchannel plate comprises a plurality of channels, each of said plurality of channels having a coating, said second generation electrons incident on said coating producing third and higher generation electrons, said amplified current signal comprising said third and higher generation electrons.

14. The tandem detector of claim 12, further comprising a second voltage source for biasing a back face of said microchannel plate with respect to said front face of said microchannel plate so as to accelerate said second generation and said third and higher generation electrons as they travel through said plurality of channels from said front face of said microchannel plate to said back face of said microchannel plate.

15. The tandem detector of claim 10, further comprising a third voltage source for biasing a front face of said solid state detector with respect to a back face of said microchannel plate so as to accelerate said third and higher generation electrons as they travel from said back face of said microchannel plate to a front face of said solid state detector.

16. The tandem detector of claim 10, further comprising a fourth voltage source for biasing a back face of said solid state detector with respect to a front face of said solid state detector to provide for collection of electron and hole pairs, said electron and hole pairs being produced by said third and higher generation electrons striking said solid state detector.

17. The tandem detector of claim 10, further comprising an insulating spacer disposed between said microchannel plate and said solid state detector.

18. The tandem detector of claim 10, further comprising a floating current monitor for registering an output signal produced by said solid state detector.

19. A method for detecting input electrons, said method comprising:
   (a) amplifying a current signal corresponding to said input electrons using a microchannel plate to produce an amplified current signal; and
   (b) detecting said amplified current signal using a solid state detector, wherein the gain of said solid state detector is adjusted based on an amplitude of said current signal;

and wherein the gain of said solid state detector is adjusted in correspondence with the gain of said microchannel plate to substantially maintain linearity of the amplification.

20. A method of claim 19, wherein the linearity of the amplification is substantially maintained over a wide dynamic range.

21. The method of claim 19, wherein said gain of said solid state detector is adjusted such as to provide a predetermined level of an output signal of said solid state detector.

* * * * *